(12) United States Patent
Gerber et al.

(10) Patent No.: US 10,537,673 B2
(45) Date of Patent: Jan. 21, 2020

(54) INTERSESSION ADAPTIVE PERITONEAL DIALYSIS FLUID REMOVAL FOR MULTIPLE SESSION OPTIMIZATION

(71) Applicant: Medtronic, Inc., Minneapolis, MN (US)

(72) Inventors: Martin T. Gerber, Maple Grove, MN (US); Christopher M. Hobot, Rogers, MN (US)

(73) Assignee: Medtronic, Inc., Minneapolis, MN (US)

( * ) Notice: Subject to any disclaimer, the term of this patent is extended or adjusted under 35 U.S.C. 154(b) by 170 days.

(21) Appl. No.: 15/666,604

(22) Filed: Aug. 2, 2017

(65) Prior Publication Data

US 2018/0043076 A1    Feb. 15, 2018

Related U.S. Application Data

(60) Provisional application No. 62/373,209, filed on Aug. 10, 2016.

(51) Int. Cl.
*A61M 1/28* (2006.01)
*G06F 19/00* (2018.01)

(52) U.S. Cl.
CPC ............ *A61M 1/282* (2014.02); *A61M 1/287* (2013.01); *A61M 2205/18* (2013.01);
(Continued)

(58) Field of Classification Search
CPC ...... A61M 1/282; A61M 1/1613; A61M 1/28; A61M 1/1696; A61M 1/287;
(Continued)

(56) References Cited

U.S. PATENT DOCUMENTS

| 4,747,822 A * | 5/1988 | Peabody | ................. A61M 1/28 128/DIG. 13 |
| 4,976,683 A | 12/1990 | Gauthier | |

(Continued)

FOREIGN PATENT DOCUMENTS

| CN | 105008893 B | 10/2015 |
| DE | 3224823 | 1/1984 |

(Continued)

OTHER PUBLICATIONS

See Advanced Renal Education Program, Cramping webpage available online at https://www.advancedrenaleducation.com/content/cramping and accessed May 3, 2019 (Year: 2017).*

(Continued)

*Primary Examiner* — Amber R Stiles
(74) *Attorney, Agent, or Firm* — Kenneth Collier; Roger Hahn

(57) ABSTRACT

The invention relates to systems and methods for optimizing a peritoneal dialysate therapy session based on one or more patient or system parameters obtained from a previous peritoneal dialysis therapy session. The systems and methods include various sensors, flow paths, and processors to adjust a peritoneal dialysis prescription for a subsequent therapy session based on data received during or after one or more previous therapy session. For example, a first peritoneal dialysis therapy session can provide data on patient or system parameters that can adjust the dialysis parameters used to deliver a subsequent peritoneal dialysis therapy session. The method can be computer implemented. The system can also include a peritoneal dialysate generation flow path.

17 Claims, 4 Drawing Sheets

(52) U.S. Cl.
CPC ............ *A61M 2205/3303* (2013.01); *A61M 2205/3324* (2013.01); *A61M 2205/3368* (2013.01); *A61M 2205/3379* (2013.01); *A61M 2230/30* (2013.01); *G06F 19/325* (2013.01); *G06F 19/3418* (2013.01); *G06F 19/3468* (2013.01)

(58) Field of Classification Search
CPC ...... A61M 2205/3303; A61M 2230/50; A61M 2230/005; A61M 2205/52; A61M 2205/3344; A61M 2205/3306; A61M 2205/3368; A61M 2205/18; A61M 2205/3324; A61M 2205/3379; A61M 2230/30; A61M 2230/62; G06F 19/3468; G06F 19/325; G06F 19/3418
See application file for complete search history.

(56) References Cited

U.S. PATENT DOCUMENTS

| | | | |
|---|---|---|---|
| 5,032,265 | A | 7/1991 | Jha |
| 5,141,493 | A | 8/1992 | Jacobsen |
| 5,643,201 | A | 7/1997 | Peabody |
| 2008/0200866 | A1 | 8/2008 | Prisco |
| 2009/0149776 | A1 | 6/2009 | Adams |
| 2010/0010425 | A1 | 1/2010 | Yu |
| 2010/0137782 | A1 | 6/2010 | Jansson |
| 2010/0312172 | A1 | 12/2010 | Hoffman |
| 2012/0029937 | A1 | 2/2012 | Neftel |
| 2012/0135396 | A1 | 5/2012 | McDevitt |
| 2012/0273354 | A1* | 11/2012 | Orhan .................. A61M 1/284 204/519 |
| 2012/0277551 | A1 | 11/2012 | Gerber |
| 2013/0186759 | A1 | 7/2013 | Lin |
| 2014/0018727 | A1 | 1/2014 | Burbank |
| 2014/0216250 | A1 | 8/2014 | Meyer |
| 2015/0148697 | A1 | 5/2015 | Burnes |
| 2016/0143774 | A1 | 5/2016 | Burnett |

FOREIGN PATENT DOCUMENTS

| | | |
|---|---|---|
| EP | 0402505 | 12/1990 |
| WO | WO1999006082 | 2/1999 |
| WO | WO2000057935 A1 | 10/2000 |
| WO | WO 20053211 | 7/2002 |
| WO | WO2009094035 A1 | 1/2008 |
| WO | 20090154955 | 12/2009 |
| WO | WO2009154955 A2 | 12/2009 |
| WO | WO 20100002830 | 1/2010 |
| WO | WO2014121161 | 8/2014 |
| WO | WO 20140121169 | 8/2014 |
| WO | WO 20150130205 | 9/2015 |
| WO | WO 20170034452 | 3/2017 |
| WO | WO 20160080883 | 5/2019 |

OTHER PUBLICATIONS

PCTUS20170146199 ISR and written opinion, dated Feb. 19, 2018.
European Search Report for App. No. 17185636.2, dated Mar. 27, 2018.
European Search Report for App. No. 17185636.2 dated Jan. 10, 2018.
PCT/US2017/025868 International Search Report dated Jun. 29, 2017.
PCT/US2017/025868 Written Opinion dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.
European Search Report for App. No. 17185638.8, dated Dec. 19, 2017.
European Search Report for App. No. 17185808.7, dated Jan. 2, 2018.
European Search Report for App. No. 17185810.3, dated Dec. 15, 2017.

\* cited by examiner

INTERSESSION ADAPTIVE PERITONEAL DIALYSIS FLUID REMOVAL FOR MULTIPLE SESSION OPTIMIZATION

CROSS-REFERENCE TO RELATED APPLICATIONS

This application claims the benefit of and priority to U.S. Provisional Patent Application No. 62/373,209 filed Aug. 10, 2016, the entire disclosure of which is incorporated by reference herein.

FIELD OF THE INVENTION

The invention relates to systems and methods for optimizing a peritoneal dialysate therapy session based on one or more patient or system parameters obtained from a previous peritoneal dialysis therapy session. The systems and methods include various sensors, flow paths, and processors to adjust a peritoneal dialysis prescription for a subsequent therapy session based on data received during or after one or more previous therapy session. For example, a first peritoneal dialysis therapy session can provide data on patient or system parameters that can adjust the dialysis parameters used to deliver a subsequent peritoneal dialysis therapy session.

BACKGROUND

Peritoneal Dialysis (PD) is a dialysis treatment that differs from Hemodialysis (HD) because blood is not removed from the body and passed through a dialyzer, but a catheter is placed in the peritoneal cavity and fluid is removed and introduced directly into the peritoneal cavity. Blood is cleaned inside the patient using the patient's own peritoneum as a type of dialysis membrane. The two primary classes of PD are Continuous Ambulatory Peritoneal Dialysis (CAPD) and Continuous Cycling Peritoneal Dialysis (CCPD) (or Automated Peritoneal Dialysis (APD)). In CAPD, dialysis is performed continuously by positioning a bag of peritoneal dialysate at shoulder level and using gravity to pull the fluid into the peritoneal cavity. The used dialysate is then drained from the cavity and discarded. The time period that the dialysate is in the cavity is called the dwell time and can range from 30 minutes to 4 hours or more. CAPD is typically performed three, four, or five times in a 24-hour period while a patient is awake. CAPD requires no cycler to deliver and remove the fluid.

The effectiveness of peritoneal dialysis therapy can depend on several factors, unique to specific patients and the session. The factors, including the number of cycles in a session, the dwell time of a cycle, the volume of a cycle, and the composition of the peritoneal dialysate, can influence patient comfort and therapy effectiveness. The timing, frequency, and composition of peritoneal dialysate used in a previous session can also impact effectiveness. Data received from a previous peritoneal dialysis session may indicate a need to change the timing, frequency, and dialysate composition for a future peritoneal dialysis sessions to optimize treatment. However, known systems provide no mechanism to make changes to subsequent peritoneal dialysis sessions based on the changing needs of a patient from one dialysis session to the next. Instead, known systems and methods are limited to users entering settings or relying on pre-programmed settings without adjustment from session to session. The known systems and methods must rely on pre-set settings because they lack the capability to self-generate an appropriate peritoneal dialysate or adjust peritoneal dialysate based on newly received data.

Hence, there is a need for systems and methods that can modify one or more patient or dialysis machine parameters from session-to-session, or "inter-session," to optimize a course of peritoneal dialysis therapy and to improve patient comfort. There is also a need for systems and methods to generate or adjust peritoneal dialysate in accordance with any adjusted dialysate prescription based on received data. The need extends to systems and methods that can make modifications to a peritoneal dialysis prescription between peritoneal dialysis sessions to optimize future peritoneal dialysis therapy sessions. There is also a need for systems and methods to generate or adjust peritoneal dialysate in accordance with any adjusted dialysis prescription.

SUMMARY OF THE INVENTION

The first aspect of the invention relates to a computer implemented method. In any embodiment, the computer implemented method can include the steps of receiving one or more patient parameters before the start of the current peritoneal dialysis session; receiving a prior dialysis prescription from a prior peritoneal dialysis session; storing the one or more patient parameters before the start of the current peritoneal dialysis session and the prior dialysis prescription into a machine-readable storage medium for storing instructions, which when executed by a dialysis machine performs the steps of: determining a new peritoneal dialysis prescription based on adjustments of the prior peritoneal dialysis prescription based on the one or more patient parameters before the start of the current peritoneal dialysis session; and delivering the new peritoneal dialysis prescription for the current dialysis therapy to a patient in need thereof, using the dialysis machine.

In any embodiment, the one or more patient parameters can include one or more of the following: (i) patient weight loss; (ii) patient blood pressure change; (iii) fluid removal volume; (iv) patient goal; (v) effluent pH; (vi) effluent color and clarity; (vii) effluent temperature; (viii) patient posture; (ix) intersession history; (x) intraperitoneal pressure; and (xi) membrane transfer efficiency.

In any embodiment, the dialysis prescription can include at least one of (i) number of cycles; (ii) dialysate temperature; (iii) target fluid removal volume; (iv) cycle volume; (v) dwell time; (vi) osmotic agent concentration; and (vii) solute concentration.

In any embodiment, at least one patient parameter can be received from an implantable or wearable sensor.

In any embodiment, the intersession history can include one or more of a peritoneal dialysate composition, a target fluid removal volume and a fluid removal volume, a dwell time, a number of cycles, a cycle volume, a patient activity, and patient well-being.

In any embodiment, the patient well-being can include whether the patient experienced cramping during or after a previous dialysis session; and the step of adjusting the peritoneal dialysis prescription can include increasing a solute concentration of at least one solute if the patient experienced cramping during or after the previous dialysis session.

In any embodiment, the patient well-being can include whether the patient experienced edema during or after a previous dialysis session; and the step of adjusting the peritoneal dialysis prescription can include increasing an osmotic agent concentration, increasing a dwell time, and/or increasing a number of cycles if the patient experienced edema during or after the previous dialysis session.

In any embodiment, the patient parameters can include fluid removal volume; the dialysis prescription can include a target fluid removal volume; and the method can include the step of adjusting an osmotic agent concentration, a dwell time, a number of cycles, or combinations thereof, in response to a difference between the fluid removal volume and the target fluid removal volume.

In any embodiment, the step of determining a new peritoneal dialysis prescription can include the step of increasing an osmotic agent concentration, increasing a dwell time, and/or increasing a number of cycles if the fluid removal volume is less than the target fluid removal volume; and the step of decreasing an osmotic agent concentration, decreasing a dwell time, and/or decreasing a number of cycles if the fluid removal volume is greater than the target fluid removal volume.

In any embodiment, the step of determining a new peritoneal dialysis prescription can include the step of reducing an osmotic agent concentration, reducing a dwell time, and/or reducing a number of cycles if the patient blood pressure change exceeds a predetermined threshold.

In any embodiment, the method can include the steps of the steps of receiving an effluent pH from a first dialysis session; receiving an effluent pH from at least a second dialysis session; trending the effluent pH over the first and second dialysis sessions; and providing an alert if the trend of effluent pH decreases by greater than a predetermined threshold.

In any embodiment, the fluid removal volume can be determined by the patient weight loss.

In any embodiment, the method can include the steps of receiving an effluent color and clarity from a first dialysis session; receiving an effluent color and clarity from at least a second dialysis session; trending the effluent color and clarity over the first and second dialysis sessions; and providing an alert if the trend of effluent color and clarity changes by greater than a predetermined threshold.

In any embodiment, the method can include the steps of receiving the intraperitoneal pressure from a first dialysis session; receiving the intraperitoneal pressure from at least a second dialysis session; trending the intraperitoneal pressure over the first and second dialysis sessions; and the step of determining a new peritoneal dialysis prescription can include increasing a dwell time if the intraperitoneal pressure decreases between the first and second dialysis sessions.

In any embodiment, the step of delivering peritoneal dialysis therapy to a patient can include controlling the movement of fluid from a water source to an infusion line of an integrated cycler in a peritoneal dialysate generation flow path; controlling the movement of fluid from one or more concentrate sources to the peritoneal dialysate generation flow path to generate a peritoneal dialysate; sterilizing the peritoneal dialysate with a sterilization module; infusing the peritoneal dialysate into a patient with the integrated cycler; and removing the peritoneal dialysate from the patient through an effluent line.

The features disclosed as being part of the first aspect of the invention can be in the first aspect of the invention, either alone or in combination.

The second aspect of the invention is drawn to a system. In any embodiment, the system can include a peritoneal dialysate generation flow path having (i) a water source fluidly connectable to the peritoneal dialysate generation flow path; (ii) one or more water purification modules fluidly connectable to the peritoneal dialysate generation flow path; (iii) one or more concentrate sources fluidly connectable to the peritoneal dialysate generation flow path; the concentrate source containing one or more solutes and including at least an osmotic agent source and an ion concentrate source; (iv) at least one concentrate pump; the concentrate pump controlling the movement of fluid from the concentrate sources to the peritoneal dialysate generation flow path; and (v) a sterilization module fluidly connectable to the peritoneal dialysate generation flow path; an integrated cycler fluidly connected to the peritoneal dialysate generation flow path; the integrated cycler having at least an infusion line and an effluent line; and a processor; the processor performing the method of the first aspect of the invention, and controlling the concentrate pump and integrated cycler based on the dialysis prescription.

In any embodiment, the system can have at least one pump positioned in the infusion line and effluent line; the pump in communication with the processor.

In any embodiment, the processor can control the pump to infuse peritoneal dialysate from the infusion line into a peritoneal cavity of a patient based on the dialysis prescription.

In any embodiment, the processor can have one or more input/output interfaces for receiving the one or more patient parameters.

In any embodiment, the system can include a peritoneal dialysate regeneration module fluidly connected to the effluent line and the peritoneal dialysate generation flow path.

The features disclosed as being part of the second aspect of the invention can be in the second aspect of the invention, either alone or in combination.

DETAILED DESCRIPTION OF THE INVENTION

Figures 1, 2:
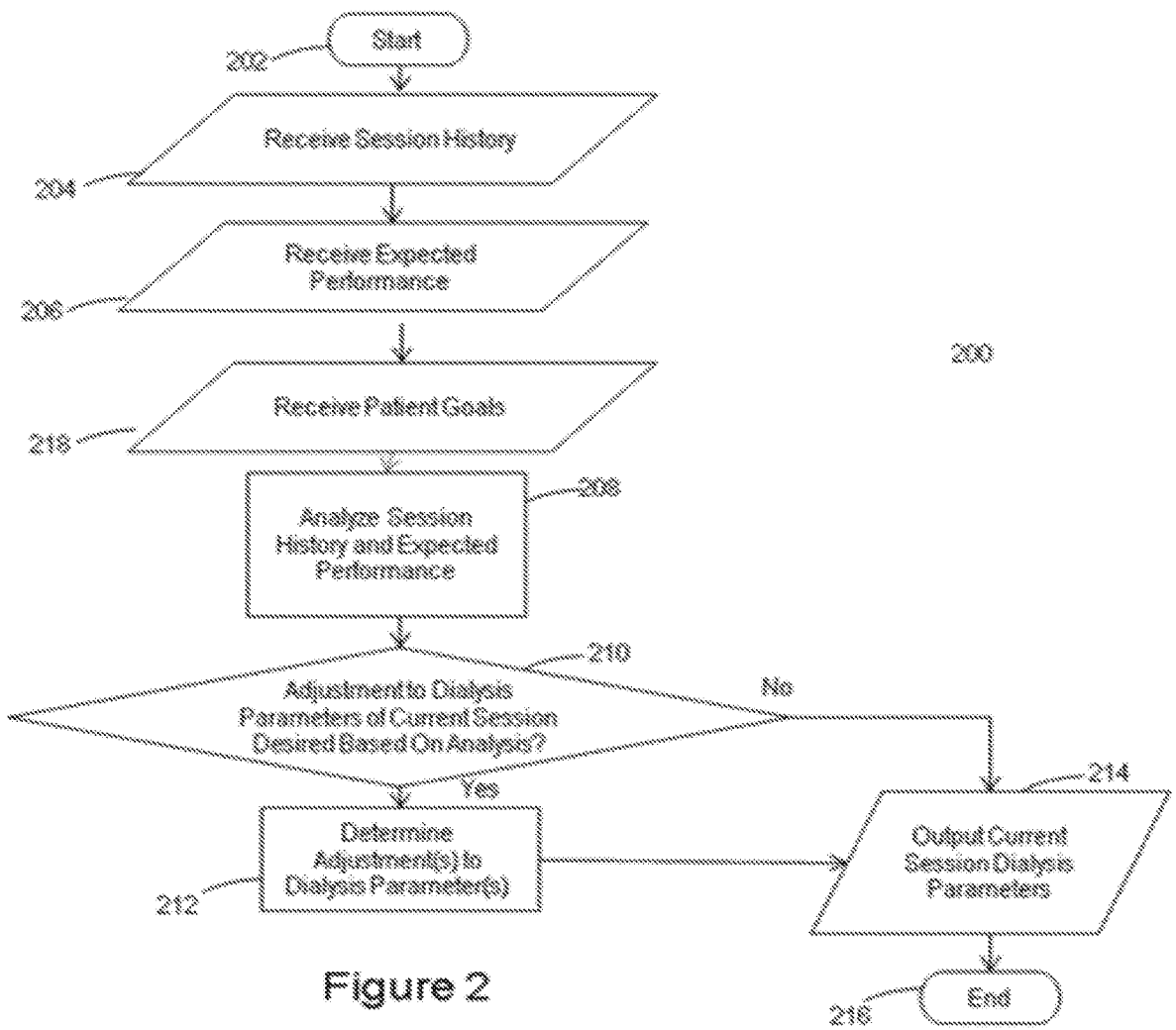
FIG. 1 shows different cycle times and number of cycles that can be set in a dialysis prescription.
FIG. 2 is a flow chart illustrating a method for adjusting a peritoneal dialysis prescription based on inter-session history.

Unless defined otherwise, all technical and scientific terms used generally have the same meaning as commonly understood by one of ordinary skill in the art.

The articles "a" and "an" are used to refer to one or to over one (i.e., to at least one) of the grammatical object of the article. For example, "an element" means one element or over one element.

The terms "adjusting," to "adjust," or "adjustment" refer to changing any parameter of a peritoneal dialysis session, including changing the concentration of one or more solutes, the temperature, the dwell time, and the number of cycles.

The terms "alert," "providing an alert," or to "provide an alert" refer to any audio, visual, or tactile indication of a particular state of a system or patient.

The term "communication" refers to an electronic or wireless link between two components.

The term "comprising" includes, but is not limited to, whatever follows the word "comprising." Use of the term indicates the listed elements are required or mandatory but that other elements are optional and may be present.

The term "computer implemented" refers to a process or set of steps carried out by a processor, computer, or any other electronic system.

The term "concentrate pump" refers to a pump positioned to control the movement of fluid between a concentrate source and a peritoneal dialysate generation flow path.

A "concentrate source" is a source of one or more solutes. The concentrate source can have one or more solutes with a solute concentration greater than the solute concentration to be used for dialysis. The concentrate in the concentrate source can also be lower than the solute concentration generally used in dialysis for generation of low concentration dialysate.

The term "consisting of" includes and is limited to whatever follows the phrase "consisting of" The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The phrase "controlling the movement of fluid" or to "control the movement of fluid" refers to directing fluid through a flow path, container, receptacle, or reservoir of any type.

The term "cramping" refers to an involuntary contraction of the muscles.

The term "cycle volume" refers to a volume of dialysate infused into a patient during a peritoneal dialysis cycle.

The terms "delivering peritoneal dialysis therapy" or to "deliver peritoneal dialysis therapy" refer to the infusion of peritoneal dialysate having into a patient and removal or drainage of the peritoneal dialysate from the patient in accordance with specified dialysis parameters.

The term "dialysate temperature" refers to the temperature of a peritoneal dialysate to be infused into a patient.

A "dialysis prescription" or "peritoneal dialysis prescription" refers to the set parameters of a peritoneal dialysis session or cycle, including the concentration of one or more solutes in the dialysate, the temperature, the dwell time, and the number of cycles in a session.

The term "dwell time" refers to the amount of time elapsed between infusion of peritoneal dialysate into a patient and drainage of the peritoneal dialysate out of the patient.

The term "edema" refers to a condition characterized by an excess of watery fluid collecting in the cavities or tissues of the body.

The term "effluent" or "peritoneal dialysate effluent" refers to fluid removed from the peritoneal cavity of a patient during peritoneal dialysis therapy.

The term "effluent clarity" refers to the percentage of light shined on a fluid removed from the peritoneal cavity of a patient that passes through the fluid.

The term "effluent color" refers to the wavelength(s) of light absorbed or transmitted by a fluid removed from the peritoneal cavity of a patient.

The term "effluent line" refers to a fluid connector for removing fluid from a peritoneal cavity of a patient. The term "effluent line" can also refer to a combined effluent and infusion line.

The term "effluent pH" refers to a measure of the hydrogen ion concentration in fluid removed from a patient.

The term "effluent temperature" refers to the temperature of fluid removed from the peritoneal cavity of a patient.

The term "execute" means to carry out a process or series of steps.

A "fluid" is a liquid substance optionally having a combination of gas and liquid phases in the fluid. Notably, a liquid can therefore also have a mixture of gas and liquid phases of matter.

The term "fluid removal volume" refers to the net volume of fluid removed from a patient during a peritoneal dialysis cycle. The fluid removal volume is equal to the difference between the amount of peritoneal dialysate infused into the patient and the amount of effluent removed from the patient with full draining.

The term "fluidly connectable," "fluidly connected," or "fluid connection" "fluidly connectable" or "fluidly connected" refers to the ability to pass fluid, gas, or mixtures thereof from one point to another point. The two points can be within or between any one or more of compartments, modules, systems, and components, all of any type.

The term "generate" refers to the creating of a substance or solution from constituent parts.

The term "implantable sensor" describes a device, component or module intended to be totally or partially introduced, surgically or medically into a mammalian body, or by medical intervention that remains after the procedure and can sense one or more patient physiological parameters.

The term "infuse peritoneal dialysate" refers to the movement of peritoneal dialysate into the peritoneal cavity of a patient.

An "infusion line" is a fluid line for carrying peritoneal dialysate into a body cavity or part of a patient such as a peritoneal cavity. The term "infusion line" can also refer to a combined effluent and infusion line.

The term "input/output interface" or "I/O" refers to a module of a processor or computing system that allows data to be received by the processor or computing system and provided by the processor or computing system. The input/output interfaces can automatically receive and provide data from sensors, or can receive data manually input through the interface, such as by a keyboard.

The term "instructions" refers to digital information that, when read or executed by a computer, processor, or system, cause the computer, processor, or system to carry out a series of steps.

The term "intraperitoneal pressure" refers to the fluid pressure within the peritoneal cavity of a patient.

The term "intersession history" refers to an electronic or machine readable record of electronic storage of dialysis parameters used and the resulting patient parameters or dialysis results from one or more previous or later peritoneal dialysis sessions. The timing and number of the session occurring in the interval from one session is non-limiting.

An "integrated cycler" is a component for movement of fluid into and out of the peritoneal cavity of a patient, wherein the integrated cycler forms a part of an overall system. For example, the integrated cycler can be contained in a housing with other components used for peritoneal dialysis and be in fluid and electrical connection with desired components.

An "ion concentrate source" refers to a source of one or more ionic compounds. The ion concentrate source can be in water or solid form. The ion concentrate source can further have one or more ionic compounds that are at a higher ion concentration greater than generally used in dialysis. In other words, an ion concentration for each particular ion can be adjusted. The concentration of the ionic compounds in the ion concentrate source can also be lower than the concentration generally used in dialysis for generation of low concentration dialysate.

The term "machine-readable storage medium" refers to any electronic device capable of storing information in a digital format for reading by a computer, processor, or other electronic device.

The term "membrane transfer efficiency" refers to the ability of water or one or more solutes to travel through a semi-permeable membrane, such as the peritoneal membrane of a patient.

The term "number of cycles" refers to the number of times peritoneal dialysate is infused into and drained from a patient in a given peritoneal dialysis session.

An "osmotic agent" is a substance dissolved in water capable of driving a net movement of water by osmosis across a semi-permeable membrane due to concentration differences of the osmotic agent on each side of the semi-permeable membrane.

The term "osmotic agent concentration" refers to the amount of one or more osmotic agents in a fluid per unit volume.

An "osmotic agent source" refers to a source of osmotic agents in solid and/or solution form. The osmotic agent source can interface with at least one other module found in systems for dialysis. The osmotic agent source can contain at least one fluid pathway and include components such as conduits, valves, filters or fluid connection ports, any of which are fluidly connectable to each other or to a fluid flow path. The osmotic agent source can either be formed as a stand-alone enclosure or a compartment integrally formed with an apparatus for dialysis for containing an osmotic agent source. The osmotic agent concentration in the osmotic agent source can be lower or higher than the osmotic agent concentration generally used in dialysis for generation of low or high osmotic agent concentration dialysate.

A "patient" or "subject" is a member of any animal species, preferably a mammalian species, optionally a human. The subject can be an apparently healthy individual, an individual suffering from a disease, or an individual being treated for a disease.

The term "patient activity" refers to any quantitative or qualitative measurement of the amount of exercised received by a patient in a given time period.

The term "patient blood pressure change" refers to a difference in blood pressure of a patient as measured at a first time and a second time.

The term "patient goal" refers to a desired peritoneal dialysis schedule, outcome, or any desired patient lifestyle factors. The patient goal can refer to an expected or desired schedule, diet, exercise, or any other patient factors.

The term "patient parameter" refers to any data without limitations that gives any medical relevant information about the health status of a patient. As used herein, a patient physiological parameter can include, but is not limited to, blood pressure, blood solute levels, posture or any other medically relevant information. For example, the physiological parameters can encompasses information such as age, weight, gender, current drug therapies, smoking habits, diet, etc.

The term "patient posture" refers to a position of the patient's body during therapy, such as sitting, standing, or lying down.

The term "patient weight loss" refers to the difference between the measured weight of a patient at a first time and at a second time.

The term "patient well being" refers to any qualitative or quantitative indications of the health or comfort of a patient.

"Peritoneal dialysate" is a dialysis solution to be used in peritoneal dialysis having specified parameters for purity and sterility. Peritoneal dialysate is different than the dialysate used in hemodialysis, although peritoneal dialysate may be used in hemodialysis.

The term "peritoneal dialysate composition" or "dialysate composition" refers to the concentration of one or more solutes in peritoneal dialysate.

A "peritoneal dialysate generation flow path" is a path used in generating dialysate suitable for peritoneal dialysis.

The term "peritoneal dialysate regeneration module" refers to a component or components capable of removing waste products from a fluid.

"Peritoneal dialysis" is a therapy wherein a dialysate is infused into the peritoneal cavity, which serves as a natural dialyzer. In general, waste components diffuse from a patient's bloodstream across a peritoneal membrane into the dialysis solution via a concentration gradient. In general, excess fluid in the form of plasma water flows from a patient's bloodstream across a peritoneal membrane into the dialysis solution via an osmotic gradient. Once the infused peritoneal dialysis solution has captured sufficient amounts of the waste components the fluid is removed. The cycle can be repeated for several cycles each day or as needed.

A "peritoneal dialysis session" is a set of peritoneal dialysis cycles performed over a time period as part of ongoing therapy. The peritoneal dialysis session can last a day or more, and can include any number of cycles.

The term "predetermined threshold" refers to a value for a parameter, set before analysis to which the analyzed parameter can be compared. Whether the analyzed parameter exceeds or does not exceed the predetermined threshold can direct or cause some action to be taken.

The term "processor" as used herein is a broad term and is to be given its ordinary and customary meaning to a person of ordinary skill in the art. The term refers without limitation to a computer system, state machine, and/or processor, designed to perform arithmetic or logic operations using logic circuitry that responds to and processes the basic instructions that drive a computer. In any embodiment of the first, second, third, and fourth invention, the terms can include ROM ("read-only memory") and/or RAM ("random-access memory") associated therewith.

The term "pump" refers to any device that causes the movement of fluids or gases by applying suction or pressure.

The term "receiving" or to "receive" means to obtain information from any source.

The term "removing" or to "remove" fluid refers to flowing fluid out of a container, system, or patient A "solute" is a substance dissolved in, or intended to be dissolved in, a solvent.

The term "solute concentration" refers to the amount of one or more substances dissolved in a fluid per unit volume.

The term "solute removal" refers to the amounts of a particular solute, such as potassium, removed from the blood of a patient during a peritoneal dialysis session.

The term "start" of a peritoneal dialysis session refers to the time at which peritoneal dialysate is infused into a patient during the first peritoneal dialysate cycle.

A "sterilization module" is a component or set of components to sterilize a fluid by removing or destroying chemical or biological contaminants.

The terms "sterilizing" or to "sterilize" refer to the removal or destruction of chemical or biological contaminants in a fluid.

The term "storing" or to "store" refers to saving electronic data or information in a machine readable medium.

The term "target fluid removal volume" is a fluid removal volume from a peritoneal dialysis session that is expected or desired.

The terms "trend" or "trending" refer to determining changes in values for one or more parameters over time.

The term "ultrafiltrate" refers to fluid that is removed from a subject by convection through the peritoneal membrane during peritoneal dialysis.

The term "ultrafiltration," as used herein, refers to the fluid removal from blood during peritoneal dialysis by passing fluid through the peritoneal membrane.

The term "water purification module" refers to a component or components capable of removing biological or chemical contaminants from water.

The term "water source" refers to a source from which potable water can be obtained.

A "wearable sensor" is a sensor capable of detecting one or more patient parameters from contact with the skin of the patient. The wearable sensor is external to the patient, but in contact with the patient such as a patch adhered to a skin surface of the patient.

Intersession Adaptive Peritoneal Dialysis

FIG. 1 is a schematic representation of an earlier peritoneal dialysis session 102 and a subsequent peritoneal dialysis session 152. By analyzing patient parameters of the earlier dialysis session 102 with, for example, expected performance, adjustments can be made to the subsequent peritoneal dialysis session 152. The system can determine that one or more patient factors (e.g., effluent solute level) should be adjusted by analyzing the earlier peritoneal dialysis session 102 prior to the start of the subsequent peritoneal dialysis session. The system can adjust the number of cycles and length of one or more cycles for the subsequent peritoneal dialysis session 152. Based on the effluent solute level, the system can determine that the subsequent session 152 should include short first and last cycles and a longer second cycle instead of four equal cycles as used in the earlier peritoneal dialysis session 102. Critical features of the systems and methods of the present invention include the capability to generate peritoneal dialysate online and infuse the peritoneal dialysate into a patient, to adjust changes to pH of a fluid, to sense a desired parameter using sensors, and to generate a sterile, neutral, dialysate using specially adapted machines and computers.

The typical number of cycles in a peritoneal dialysis session can be four. As described, the number of cycles can be varied for therapeutic effect, and can range from two to six or more cycles. The peritoneal dialysis cycle refers to the process of infusing peritoneal dialysate into a patient, dwelling the peritoneal dialysate within the peritoneal cavity of the patient, and removing the peritoneal dialysate from the peritoneal cavity of the patient. The process of filling and then draining a peritoneal cavity can also be referred to as an exchange of used and clean fluids. However, the number, length, and timing of cycles or exchanges are non-limiting. For example, Continuous Ambulatory Peritoneal Dialysis (CAPD) and Continuous Cycling Peritoneal Dialysis (CCPD) can occur on different schedules, but the process of filling and then draining the peritoneal cavity occur for both CAPD and CCPD. As such, the term cycle or exchange refers to any exchange as used for any dialysis schedule or dialysis type.

FIG. 2 is a flowchart of a computer implemented method 200 for adjusting dialysis parameters prior to the start of a current peritoneal dialysis session based on earlier session patient parameters. Instructions for carrying out any of the method or process of the present invention including the process illustrated in FIG. 2 can be stored in a machine readable medium, database, or any other suitable electronic format such as programming code. In any embodiment of the invention, a processor or suitable computer or electronic process for carrying out a set of instructions can be performed in a dialysis machine constructed to execute the set of instructions. The method 200 can begin in operation 202. In operation 204, intersession history can be received into a system for modifying dialysis parameters of a subsequent peritoneal dialysis session based on earlier session patient parameters, such as the system 500 of FIG. 5. The intersession history can be stored in a machine readable medium, database, or any other machine readable storage format. For example, the intersession history can be received as input into an I/O interface of the system. As another example, the intersession history can be received from memory of the system.

The intersession history can include patient parameters received as parameter input and/or from the one or more sensors. The intersession history can also include information automatically received by the system from the patient's electronic medical records (EMR) or electronic health record (EHR). The system can connect to the internet using an API to receive data from a patient's EMR or EHR. For purpose of the present invention, the terms EMR and EHR are used interchangeably to refer to patient data stored in a retrievable electronic format. The intersession history can be stored in an electronic or machine readable format, or electronic storage. The dialysis parameters can be any factor of a peritoneal dialysis session that can affect the health of a patient during and after dialysis including, but not limited to, occurrence of dialysis, net or given fluid removal in a cycle, fluid removal rate, concentration of one or more solutes in a peritoneal dialysate, a number of cycles in a peritoneal dialysis session, a dwell time of a cycle, temperature of the peritoneal dialysate, or any other factor used in peritoneal dialysis. The patient parameter included in the intersession history can include any data providing medically relevant information about the health status of a patient. For example, a patient physiological parameter can include, but is not limited to, blood pressure, blood solute levels, posture or any other medically relevant information. The physiological parameters can encompasses information such as age, weight, gender, current drug therapies, smoking habits, diet, etc.

In operation 206, expected performance of sessions from the intersession history can be received as input into the input output interface of the system. Optionally, the system can also receive as input one or more patient goals in operation 218. The patient goal can change throughout a given week or over an extended period of time. An example is to remove more fluid during the week to allow more flexibility in the patient fluid intake, diet, exercise level and schedule during the weekend or to allow a night off from treatment. The patient goals may be different for different days during the week to match the patient life style or physiology. For example, some patients may respond better with more fluid removed during the middle of the week. The patient goals can also include the time available for therapy, the desired volume removal, which may be more or less aggressive than the original dialysis prescription, especially working toward a weekend or special event, how the patient feels, physical activity planned/performed, diet (i.e. large meat consumption), and schedule flexibility. Another patient or physician goal could be the number of cycles performed during a session. The number of cycles could be adaptable depending on how the patient responds, or patient goals and schedule, such as the length of time the patient is asleep in CAPD. For example, some patients may respond better with a higher fluid removal volume during middle of the week. The patient or physician goals may change from session to session. The prior session history can be used to determine what adjustments to the prescription can be made in accordance with the patient goals without decreasing therapy efficacy.

In operation 208, the intersession history and the expected performance can be analyzed, along with the patient goals for subsequent dialysis sessions. In operation 210, a determination can be made regarding whether an adjustment to the dialysis parameters of the current session is desired based on the analysis performed during operation 208. One of ordinary skill in the art will recognize that multiple patient parameters can be monitored and analyzed, and that multiple dialysis parameters can be adjusted for a current session of the peritoneal dialysis session based on the analysis. Table 1 contains illustrative examples of patient parameters and dialysis parameters. One of skill in the art will understand that any combination of patient parameters can be analyzed, and that any number of dialysis parameters can be adjusted in a dialysis prescription for a subsequent cycle. The intersession history can also include patient activity or patient well-being. A low patient activity level after a previous session could indicate insufficient fluid removal, and the osmotic agent concentration could be increased, the number of cycles could be increased, and/or the dwell time can be increased to remove additional volume in a subsequent session. Patient well-being can include whether the patient experienced edema or cramping during or after a previous dialysis session. Edema or other bloating could be a sign of fluid overload and a need for a higher target fluid removal volume. Cramping could be a sign of too aggressive electrolyte removal, and the solute concentration in the dialysate increased for future sessions. Any adjustment to the dialysis prescription based on changing patient goals or patient parameters can be checked against the patient history. If a particular adjustment has already been tried for the patient and included in the patient history, the system can determine the effects of the adjustment in previous sessions. If the adjustment did not previously result in improved performance, the system can output a different adjustment to the prescription, or can output a notification that the patient goals cannot be met without a decrease in therapy efficacy. Certain parameters listed in Table 1 are related to other parameters. For example, the volume of effluent removed is equal to the volume of dialysate infused plus the net ultrafiltrate removed. Patient weight loss and the intraperitoneal pressure are also a function of the net fluid removal. The system can measure any one or more of the parameters to determine any of the other parameters. For example, the net ultrafiltrate removed can be calculated either by the volume of effluent removed minus the volume of dialysate infused, or the net ultrafiltrate removed can be calculated by the patient weight loss.

TABLE 1

| Patient Parameters | Dialysis Parameters |
|---|---|
| Patient weight loss/ultrafiltrate removed | Osmotic agent concentration, number of cycles, dwell time |
| Patient blood pressure change | Osmotic agent concentration, dwell time |
| Volume of effluent removed | Glucose, dwell time, number of cycles, pumping rate and time, cycle volume |
| Patient goal | Dwell time, cycle volume, number of cycles, dialysate composition, dialysate temperature, time to perform therapy, timing of session |
| Blood solute level | Dwell time, dialysate composition |
| Effluent solute level | Dwell time, number of cycles, dialysate composition |
| Effluent color/clarity | Number of cycles, presence of infection |
| Effluent temperature | Number of cycles, dialysate temperature, dwell time, volume, presence of infection |
| Patient posture | Cycle volume, dwell time, osmotic agent concentration |
| Intraperitoneal pressure | Cycle volume, cycle effluent removed, dialysate composition, especially osmotic agent concentration, posture, |

If in operation 210, a determination is made that an adjustment to the dialysis parameters is not desired, the method can proceed to operation 214. In operation 214, control signals implementing dialysis parameters (without adjustment) for a subsequent cycle of the current session can be transmitted to components of the system.

If in operation 210 a determination is made that an adjustment to the dialysis parameters is desired, the method can proceed to operation 212. In operation 212, an adjustment to the dialysis parameters can be determined based on the analysis performed during operation 208. The adjusted dialysis prescription can be stored in a machine readable storage medium or other suitable computer or processor for later use in peritoneal dialysis therapy. After operation 212, the method 200 can proceed to operation 214, where control signals implementing dialysis parameters (with adjustment) can be transmitted to components of the dialysis machine for delivering peritoneal dialysis therapy to the patient. After operation 214, the method 200 can proceed to operation 216 and the method 200 can end. The system can then initiate a peritoneal dialysis session using the output dialysis prescription.

The output dialysis prescription and the results from the new peritoneal dialysis session can be received and stored by the system to update the patient history. The patient history thus becomes a continuously updating patient profile that can be used for optimizing subsequent dialysis sessions. The system can learn and build a customized patient therapy profile for the patient. By continuously saving the dialysis prescription and therapy results, the system can test and observe different parameters and then make adjustments in subsequent sessions. The system can apply machine learning techniques to learn from each session for a given patient, and then apply the new parameters in a subsequent session using statistical techniques known to those of ordinary skill. For example, a naive Bayes predictor can be applied to classify any of the parameters of the present invention into classes. The classified parameters can then be reviewed and analyzed. The system can also build a patient profile, saved as the session history in the machine readable storage medium, and can adjust the dialysis prescription in response to changing patient parameters and goals. Because the patient parameters and goals can change day to day, the patient profile of action/reaction can be used to dynamically adjust the therapy to optimize therapy outcomes, meaning that effective treatment is given while meeting patient goals.

If an action is tried but is not fruitful, the system can record the results in the session history for the patient and avoid the action in subsequent sessions. For example, a patient beginning a dialysis session at a heavier weight than normal could indicate additional fluid build up since the last dialysis session. A patient at any weight over normal could be indicative of fluid buildup, including a patient at between 0.2 and 1.5 kg, between 0.2 and 0.5 kg, 0.2 and 1.0 kg, or 0.5 and 1.5 kg overweight. In response to a patient at a heavier than normal weight, the system can adjust the dialysis prescription to remove additional fluid, such as by increasing the dwell time. If the increased dwell time does not result in sufficient fluid removal, the system can record the unsuccessful attempt in the patient history. The next time the patient begins a session at a higher than normal weight, the system will know that increasing the dwell time for the patient does not result in a more positive outcome. In subsequent sessions, the system can attempt other adjustments, such as increasing the osmotic agent concentration when the patient begins at a higher than normal weight. Because the patient history and profile include both successful and unsuccessful results, the system can learn which adjustments provide improved outcomes depending on the patient parameters. The system can adjust future dialysis sessions by placing a higher priority on adjustments that result in positive outcomes than adjustments that are not successful.

Figure 3:
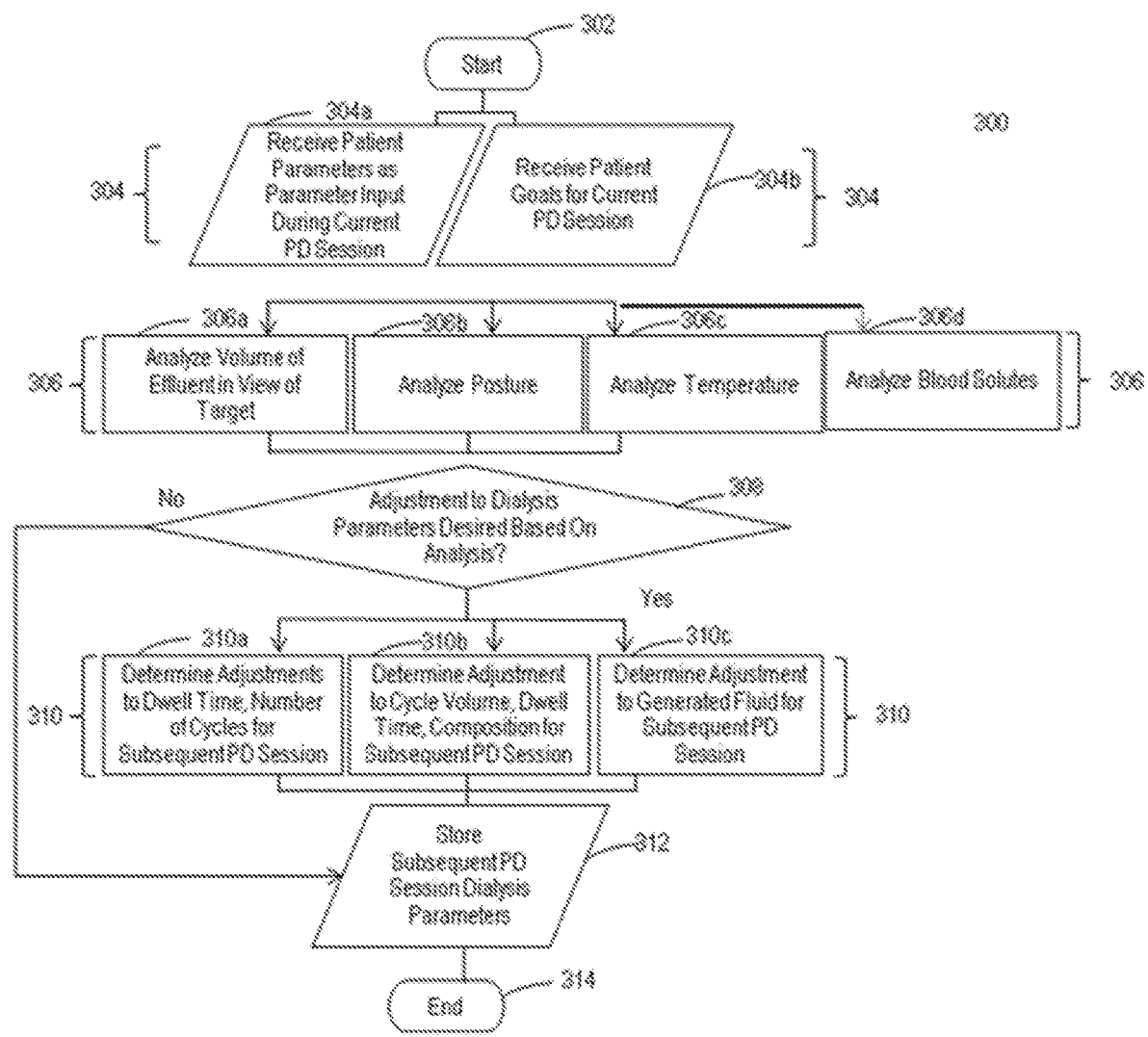
FIG. 3 is a flow chart illustrating a method of adjusting a peritoneal dialysis prescription based on received patient parameters.

FIG. 3 is a flowchart of a computer implemented method 300 for monitoring patient parameters to adjust dialysis parameters prior to the start of a peritoneal dialysis session. Instructions for carrying out the method illustrated in FIG. 3 can be stored in a machine-readable storage medium or other suitable computer storage device such as a processor or programmable code. A processor or other suitable computer in a dialysis machine can execute the instructions to perform the described method. Alternatively, the instructions can be transmitted wireless or over the internet to the dialysis machine, wherein the machine will then carry out. The method 300 can begin in operation 302. A peritoneal dialysis session can be initiated by a system for modifying dialysis parameters of a subsequent peritoneal dialysis session based on earlier session patient parameters.

In operation 304, one or more patient parameters can be received during or after the current peritoneal dialysis session and stored in a machine-readable storage medium or other suitable computer storage device such as a processor or programmable code. For example, patient parameters can be received as parameter input into a computing device of the system in operation 304a either from one or more sensors, or through an input/output interface in the computing system. For example, a patient posture (laying down, sitting up) can be entered manually into the system and received into the computing device as parameter input. Alternatively, an implanted or wearable accelerometer can transmit the patient posture to the system. An example of an implantable accelerometer is the Medtronic Reveal LINQ or catheter based accelerometers. A net or given fluid removal volume during the current session can be measured using a flow sensor of the system and received into the computing device. The net or given fluid removal volume can be directly measured by flow sensors in an effluent line of a peritoneal dialysis cycler, or calculated based on a patient weight loss during therapy. Patient weight loss, which indicates the ultrafiltration amount, can be measured by having the patient step on a scale prior to and after therapy. The difference in the patient weight before and after therapy can be manually entered into the system, or automatically received by the system from a scale in electronic communication with the processor. The scale data can be transmitted wirelessly, by the internet, or cable. Effluent temperature removed during the current PD session can be measured using a temperature sensor along the effluent line. Conductivity sensors, ion selective electrodes, or other suitable sensors can be positioned in an effluent line to measure the concentration of one or more solutes in the effluent. A refractive index sensor or other suitable sensor can determine the glucose or other osmotic agent concentration. In operation 304b, patient goals for the current peritoneal dialysis session can be received by the system and stored in the machine-readable storage medium.

In operation 306, the one or more parameters can be analyzed, optionally in view of one or more target values and the patient goals. Multiple instances of operation 306 are depicted in FIG. 3. For example, in operation 306a, the net or given fluid removal volume can be analyzed in view of a target fluid removal volume set in a dialysis prescription stored in a machine-readable storage medium or other suitable computer storage device such as a processor or programmable code. As another example, in operation 306b, a patient posture during the peritoneal dialysis session can be analyzed. In operation 306c, an effluent temperature can be analyzed. In operation 306d, patient blood solute levels can be analyzed. Each of the patient parameters and system parameters described make up an intersession history, along with actual results achieved, such as the fluid volume removal from the prior session. The intersession history and patient goals can be used to adjust the peritoneal dialysis prescription, stored in the machine-readable storage medium, for subsequent dialysis sessions. The dialysate temperature can also be adjusted to match the effluent temperature to increase patient comfort. Small differences between the patient's body temperature and the infused dialysate, including differences of a tenth of a degree or less, can result in significant discomfort for the patient. An increase in effluent temperature may also indicate an infection, and an alert provided to the physician for medical intervention. The effluent temperature can be measured on the first cycle, which can then be used to determine whether there is potential infection as determined by an elevated temperature, or whether to modify the dialysate temperature to match the patient temperature. The patient weight can also be received by the system, and compared to the patient weight after the previous session to estimate fluid buildup in the patient. Weight loss in prior session can be used to modify dialysate composition, the number of cycles, and/or the cycle volume for future sessions because patient weight loss can be an indicator of the fluid removal volume from the previous session. The dialysate composition includes both the osmotic agent concentration and the solute concentration in the dialysate. Patient goals can also be received by the system.

In operation 308, a determination can be made whether an adjustment to the dialysis parameters in a subsequent session is desired based on the analysis performed of the intersession history and the patient goals during operation 306. If the net or given fluid removal volume is lower than the target net or given fluid removal volume, various other parameters such as an osmotic agent concentration, can be increased in a subsequent session. Alternatively, dwell time could be increased, and/or a number of cycles could be increased in a subsequent session. The changes can be compared to the patient goals, such as fewer cycles, and the system can determine the necessary adjustments to the prescription to achieve the target net or given fluid removal volume while meeting the patient goals. Conversely, if the volume of the net or given fluid removal volume is higher than the target net or given fluid removal volume, the osmotic agent concentration can be decreased in a subsequent session, dwell time could be decreased in a subsequent session, and/or a number of cycles in a subsequent session could be decreased.

The patient blood solutes can be profiled to control the ultrafiltration rate and solute removal. For example, if a patient has a high blood potassium level, a high ultrafiltration rate may not be desirable, as a high ultrafiltration rate with high potassium can cause irregular heartbeats or other issues. The system can adjust the osmotic agent concentration in the dialysate to use a lower dextrose concentration for the early cycles to reduce the ultrafiltration volume in the earlier cycles, controlling the mass of potassium removed, which is a function of the ultrafiltration volume and potassium blood concentration. As the concentration of potassium decreases during the early cycles of the peritoneal dialysis session, the ultrafiltration volume can be increased by increasing the osmotic agent concentration so that the overall fluid removal goals can be met, while keeping the removal rate of potassium more constant. The same approach can also be used to clear toxins that are primarily stored in the intracellular or extracellular fluid compartments, where transport from intracellular or extracellular compartment into the blood volume is the limiting factor in clearance. For such molecules increasing the ultrafiltration rate over a dialysis session may be advantageous to allow sufficient time for the toxins to transfer into the blood compartment and maximize clearance. The ability of the system illustrated in FIG. 5 to manipulate the osmotic agent concentration for each cycle makes changing the osmotic agent concentration cycle-to-cycle possible. The results on solute removal and overall ultrafiltration achieved with cycle-to-cycle osmotic agent changes can be recorded in the patient history.

As another example, if the patient posture is upright during the dialysis session, adjustments to cycle volume, dwell time, and/or composition, including the osmotic agent concentration and solute concentration, for a subsequent session can be desirable. For example, a patient sleeping upright could indicate excess fluid and trigger a larger target fluid removal volume, which can be achieved by increasing an osmotic agent concentration, increasing the dwell time, or increasing the number of cycles. Further, an upright patient may have less of the peritoneum in contact the fluid when standing, resulting in lower fluid transport. An adjustment to the peritoneal dialysis prescription to increase the dwell time can be used to compensate for the patient posture. Using the intersession history, the system can learn the necessary increase in dwell time to compensate for the patient posture for the particular patient. As another example, an effluent temperature can be determined, and adjustments made to the peritoneal dialysis prescription based on the effluent temperature, which is correlated with patient body temperature. In some examples, patient comfort can be improved by adjusting the dialysate temperature to match the natural circadian rhythms of the patient. During sleep, a patient's body temperature may drop 1-2 C over the night. A patient history can be obtained, for example, by monitoring the patient's temperature over time to develop patient specific cycles. The temperature profile for each peritoneal dialysis cycle can be adjusted to match the patient's natural temperature cycles. Alternatively, the effluent temperature con be measured and the temperature of the next cycle can be set to match the temperature of the effluent of the previous cycle. Varying the peritoneal dialysate fluid temperature to match natural circadian temperature rhythms may improve sleep quality and maintain efficiency of cellular processes that are regulated by circadian rhythms. The fluid removal volume and patient well-being factors can be correlated to temperature, and the peritoneal dialysis prescription in subsequent sessions adjusted in light of the correlation. See, for example, "Effect of Dialysate Temperature and Flow Rate on Peritoneal Clearance." Melvin Gross, MD; Harold P. McDonald Jr., MD, JAMA. 1967; 202(4):363-365 (doi: 10.1001/jama.1967.03130170163035). Clearance can be 35% higher when PD fluid was infused at 37° C. compared to 20° C.

One of ordinary skill in the art will recognize that the analysis of operation 306 can be performed in a number of ways. For example, rather than determining if the patient parameter meets a condition relative to a target, a determination can be made whether the patient parameter fails to meet a condition relative to a target. As another example, a determination can be made whether the target meets or fails to meet a condition relative to the patient parameter. Variations are considered as equivalent approaches under the general concept of operation 306.

If in operation 308 a determination is made that an adjustment to the dialysis prescription is not desired, or if the adjustment to the dialysis prescription would be outside of a predefined safety or comfort range, the method can proceed to operation 312. In operation 312, control signals delivering peritoneal dialysis therapy with the dialysis prescription (without adjustment) for a subsequent session can be stored in a machine-readable storage medium of the system for use by components of the system.

If in operation 308, a determination is made that an adjustment to the dialysis parameters is desired, the method can proceed to operation 310. In operation 310, an adjustment to the peritoneal dialysis prescription can be determined based on the analysis performed during operation 306. Multiple instances of operation 310 are depicted in FIG. 3. For example, in the net or given removal volume example, an adjustment to one or more of osmotic agent concentration for a subsequent session, a dwell time for a subsequent session and a number of a subsequent session can be determined in operation 310a. Alternatively, for patient posture, an adjustment to one or more of cycle volume, dwell time, and composition for cycles of a subsequent session can be determined in operation 310b. Alternatively, in operation 310c, for effluent temperature, an adjustment to the temperature of peritoneal dialysate infused into the patient in a subsequent session can be determined. In operation 312, control signals implementing dialysis parameters (with adjustment) for a subsequent session can be stored in a machine-readable storage medium of the system for use by components of the system in delivering peritoneal dialysis therapy during a subsequent session. After operation 312, the method 300 can proceed to operation 314, and the method 300 can end.

Figure 4:
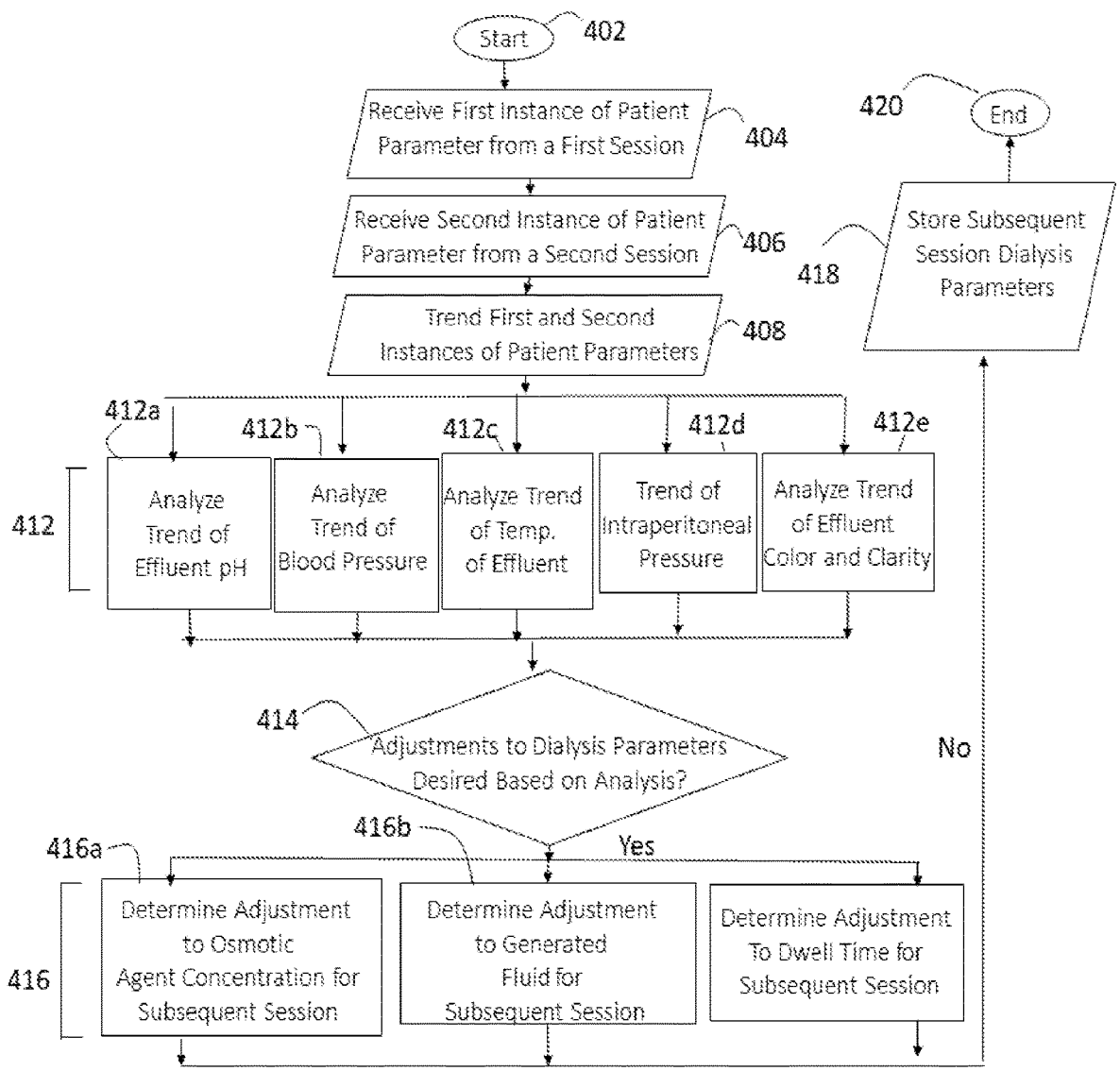
FIG. 4 is a flow chart illustrating a method of adjusting a peritoneal dialysis prescription based on a trend of one or more patient parameters.

FIG. 4 is a flowchart of a computer implemented method 400 for monitoring patient parameters during a peritoneal dialysis session to adjust dialysis parameters for a subsequent peritoneal dialysis session based on intersession history for the patient. Instructions for carrying out the method illustrated in FIG. 4 can be stored in a machine-readable medium. A processor in a dialysis machine can execute the instructions to perform the described method. The method 400 can begin in operation 402. In operation 404, a first set of patient parameters from a first peritoneal dialysis session can be received by the system and stored in a machine-readable storage medium. In operation 406, a second set of patient parameters from a second peritoneal dialysis session can be received by the system and stored in a machine-readable storage medium. As described, the system can receive the patient parameters automatically from one or more sensors, from a patient's electronic medical records, or the patient parameters can be manually input into the system through an input/output interface.

In operation 408, the system can create a trend of the patient parameters from the first and second dialysis sessions. The trend can be created from any number of previous dialysis sessions, with increasing accuracy as the number of sessions increases. One of skill in the art will understand that any number of dialysis sessions can be included in the intersession history, and the invention is not limited to analyzing a trend from only two dialysis sessions. The effectiveness of the system in optimizing subsequent dialysis sessions will increase with an increasing number of dialysis sessions provided in the intersession history.

In operation 412, the trend the patient parameter can be analyzed. Multiple instances of operation 412 are depicted in FIG. 4. For example, in operation 412a, a trend of patient blood pressure changes from previous dialysis sessions are analyzed. As another example, in operation 412b, a trend of effluent temperature measurements can be analyzed to determine correlations to other parameters, such as generated fluid temperature. In step 412c, a trend of intraperitoneal pressure measurements can be analyzed to determine any necessary changes to the dwell time. Additional factors, such as the pH of the effluent removed from the patient can also be trended in operation 412d, or the optical effluent color and clarity of the effluent can be trended in operation 412e.

In operation 414, a determination can be made whether an adjustment to the dialysis parameters of the previous dialysis prescription and stored in a machine-readable storage medium is desired based on the analysis performed during operation 412. For example, a patient blood pressure change is that is decreasing or trending low over the previous dialysis sessions could indicate that the rate of ultrafiltration is too high. The change in patient blood pressure is a function of the ultrafiltration amount and the ultrafiltration rate, and is influenced by the dwell time, the number of cycles, and the net or given fluid removal volume. Removing ultrafiltrate from the patient at too high a rate or too high a volume can lead the patient into a hypotensive episode. The system can balance the overall rate of removal of ultrafiltrate and total ultrafiltrate volume removed. To balance the rate and volume of ultrafiltrate removal, the system can adjust the osmotic agent concentration, the dwell time, the number of cycles, and/or the cycle volume. As such, the system can optimize each of the dialysis parameters for a subsequent cycle to maintain a more steady blood pressure. Conversely, an increasing trend could suggest fluid removal is insufficient and the osmotic agent concentration could be increased to compensate. As another example, if the temperature of effluent removed over the intersession history shows a decrease below a threshold, a temperature of a dialysate temperature for cycles of a subsequent session can be increased. Alternatively, temperature of effluent removed over the intersession history can be compared against performance data for fluid volume removal and correlated, allowing for fine tuning or optimization of temperature for patient comfort and/or performance in subsequent sessions. Further, if the temperature of effluent removed is increased over the intersession history temperatures, the increase can indicate a patient health issue such as the presence of an infection or disease. As another example, first and second instances of intraperitoneal pressure can indicate peritoneum "fullness" to manage cycle volume. The intraperitoneal pressure can be determined by pressure sensors in the infusion or effluent lines. During filling, a high pressure may lead to patient discomfort, as too much dialysate in the peritoneal cavity can lead to the patient feeling bloated or distended. In response to a high pressure, the cycle volume can be decreased for patient comfort. The cycle volume will depend on patient size but can be expected to be 0.5 to 3 liters/cycle. For a typical adult the cycle volume is about 1.5 L. When varying the cycle volume for therapeutic effect, the cycle volume can be varied by any amount, including by 0.1 L to 1 L. Varying the cycle volume can be performed in small or large steps depending on how far the patient parameters are from a therapeutic target value. The practical upper limit of the cycle volume is patient dependent, but can be considered approximately 3.5 to 4 L. Pressure can indicate incomplete removal of previous cycle volume. As such, input fluid for cycles in a subsequent session can be adjusted to compensate for the incomplete removal. Further, an increasing trend in intraperitoneal pressure could indicate peritonitis as higher pressure is correlated with night enteric peritonitis and higher patient mortality. Changes in intraperitoneal pressure over multiple sessions, such as an increasing trend in intraperitoneal pressure, may indicate degradation in peritoneal membrane performance due to the production of less ultrafiltrate. In some examples, early detection of changes in intraperitoneal pressure, such as can enable medical intervention such as infection treatment or dialysate composition changes to reduce inflammation before the permanent damage to the peritoneal membrane.

A decreasing intercycle intraperitoneal pressure trend line can result in added time required for draining the peritoneal cavity of the patient. The dwell time can be increased by the system to compensate for the longer fill and drain times. An intercycle decrease in intraperitoneal pressure could also indicate membrane transport properties of the peritoneum are waning, and less ultrafiltrate is being removed from the patient. In response, the cycle volume can be increased. If in operation 414, a determination is made that an adjustment to the dialysis parameters is not desired, the method can proceed to operation 418. In operation 418, control signals implementing dialysis parameters (without adjustment) for a subsequent session can be stored in the machine-readable storage medium for use by components of the system in delivering peritoneal dialysis therapy to a patient. A decreasing pH trend line over one or more sessions could indicate an infection in the patient, or poor membrane transfer efficiency. Membrane transfer efficiency can be determined by either 1) the ultrafiltrate removal volume (taking into account cycle parameters such as cycle number, solution, dwell time, etc.) and/or 2) the conductivity/composition of the effluent sampled from the patient (an indicator of the ion transport across the peritoneum). By trending the changes in effluent pH and/or effluent conductivity, the membrane transfer efficiency can be obtained and trended. In response to a decreasing membrane transfer efficiency, the osmotic agent concentration can be increased, the dwell time increased, and/or the number of cycles increased. An intersession change in pH may indicate a change in the acidotic status of the patient, and can be used to modify the dialysate, patient medications, or diet. Change in conductivity vs. time can also indicate when the dwell should end and new fluid cycled (dwell time). Osmolality of the fluid could also indicate when the dwell should be end and new fluid cycled. The cycle volume could be used to adjust future cycles (time, volume, composition).

The effluent pH can be measured by a pH sensor in the effluent line, or alternatively, a small amount of fluid can be removed from the system for separate pH measurement. If the trend in effluent pH crosses a predetermined threshold, the system can provide an alert to the patient or health care professional indicating a possible infection, a failing peritoneum, or a change in the patient acidotic state. Changes in the optical color of the effluent or clarity of the effluent could also indicate an infection. Growth of bacteria in the peritoneum, infiltration of white blood cells into the peritoneum in response to the infection, and leakage of red blood cells could all be signs of infection or failing peritoneum and can be determined from a trend of the optical color and clarity of the effluent removed from a patient over multiple sessions. If the trend in effluent color or effluent clarity crosses a predetermined threshold, the system can provide an alert to the patient or health care professional indicating a possible infection. The effluent color and clarity can be determined using a spectroscope. A sample of filtrate from the effluent line can be removed and analyzed using an off-line or integrated spectroscope to determine the color and clarity of the filtrate.

If in operation 414, a determination is made that an adjustment to the dialysis parameters is desired, the method can proceed to operation 416. In operation 416, an adjustment to the dialysis parameters can be determined based on the analysis performed during operation 412 and the adjusted dialysis prescription stored in a machine-readable storage medium. Multiple instances of operation 416 are depicted in FIG. 4. For blood pressure, an adjustment to an osmotic agent concentration can be determined in operation 416a for a subsequent session. Alternatively, for effluent temperature, an adjustment to peritoneal dialysate fluid temperature can be determined in operation 416b. Alternatively, in operation 416c, for intraperitoneal pressure, an adjustment to dwell time can be determined. In response to a change in the acidotic status of the patient, the system can adjust the dialysate composition, or recommend changes in patient medication or diet. After operation 416, the process can proceed to operation 418.

In operation 418, control signals implementing dialysis parameters (with adjustment) for a subsequent session can be stored in a machine-readable storage medium for use by components of the system in delivering peritoneal dialysis therapy to the patient. After operation 418, the method 400 can proceed to operation 420 and the method can end.

Peritoneal Dialysate Generation and Integrated Cycler

Figure 5:
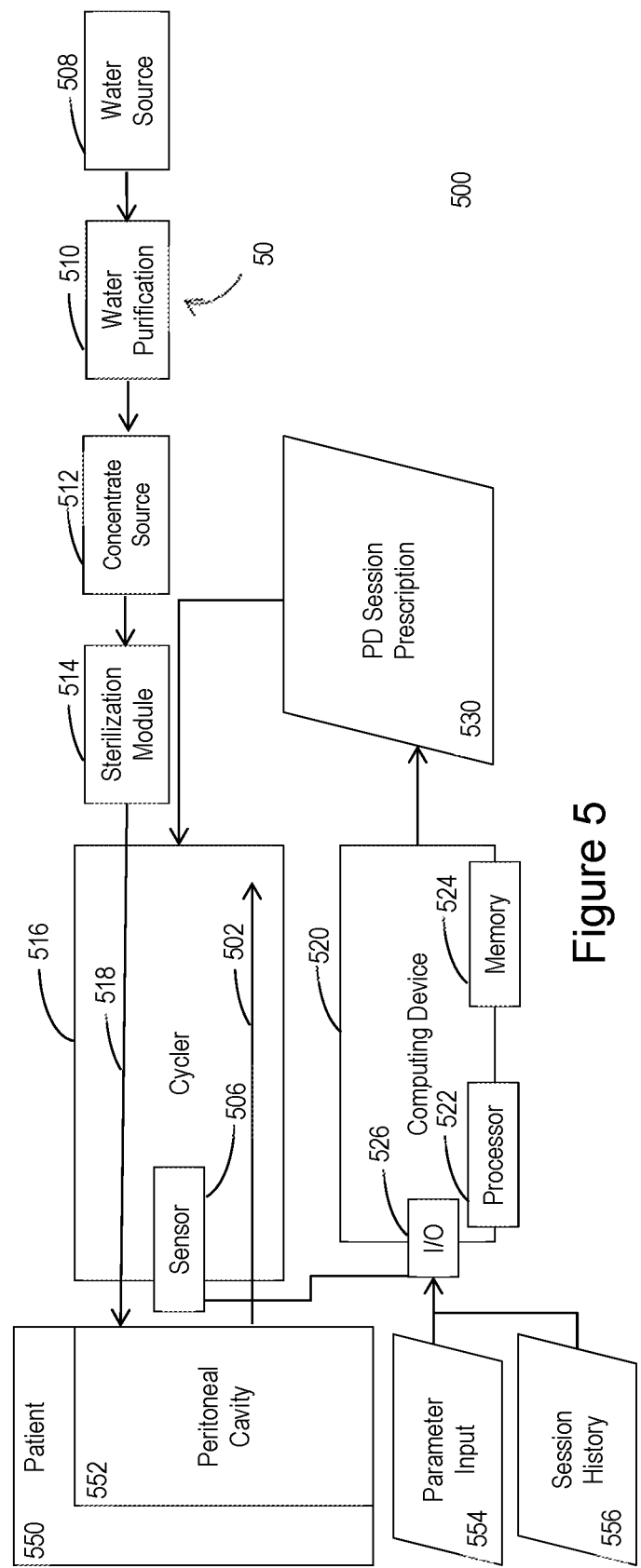
FIG. 5 is a non-limiting example of a system for adjusting a peritoneal dialysis prescription and delivering therapy.

FIG. 5 shows a system 500, which is part of a dialysis machine, for monitoring patient parameters during a peritoneal dialysis session to make modifications within the same peritoneal dialysis session. One or more patient parameters can be obtained by the system 500 during the previous peritoneal dialysis sessions. The one or more patient parameters can be analyzed. One or more dialysis parameters in a dialysis prescription can be adjusted for a subsequent session based on the analysis.

The system 500 can include a peritoneal dialysate effluent line 502, a peritoneal dialysate infusion line 518, a peritoneal dialysate generation flow path 504, one or more optional sensors 506 positioned in one or both of the peritoneal dialysate effluent line 502 and the peritoneal dialysate generation flow path 504, and a computing device 520. The computing device 520 can include the machine readable instructions, which when executed by the dialysis machine perform the methods described with reference to FIGS. 1-4 and generate the peritoneal dialysate, as described. One of skill in the art will understand that one or more implantable sensors in the patient can be included, such as an implantable accelerometer or blood pressure monitor or cuff. The peritoneal dialysate effluent line 502 can be fluidly connected to a waste reservoir (not shown) to collect effluent.

The peritoneal dialysate generation flow path 504 can include a water source 508, one or more water purification modules 510, a concentrate source 512, a sterilization module 514, and an integrated cycler 516. The concentrate source 512 can contain one or more solutes. The water source 508, water purification module 510, concentrate source 512, sterilization module 514, and integrated cycler 516 can be fluidly connectable to the peritoneal dialysate generation flow path 504. The integrated cycler 516 can include the effluent line 502, an infusion line 518, and one or more pumps for infusing peritoneal dialysate into the peritoneal cavity 552 of the patient 550 and removing fluid from the peritoneal cavity 552 of the patient 550. The one or more pumps of the integrated cycler 516 can be in communication with the processor for controlling the number movement of fluid through the integrated cycler 516 and controlling the cycles, cycle volume, and fill and drain rates, as described, to deliver peritoneal dialysis therapy to a patient in accordance with the dialysis prescription stored in the computing device 520. One or more processors 522 can adjust the dialysis prescription for a current or subsequent session. For example, the processor 522 can control the movement of fluid from the concentrate source 512 to the peritoneal dialysate generation flow path 504 based on the monitored patient parameters.

The water source 508 can be a non-purified water source, such as tap water, wherein the water from the water source 508 can be purified by the system as described. A non-purified water source can provide water without additional purification, such as tap water from a municipal water source, water that has undergone some level of purification, but does not meet the definition of "purified water" provided, such as bottled water or filtered water. The water source can contain water meeting the WHO drinkable water standards provided in *Guidelines for Drinking Water Quality*, World Health Organization, Geneva, Switzerland, 4th edition, 2011. Alternatively, the water source 508 can be a source of purified water, meaning water that meets the applicable standards for use in peritoneal dialysis without additional purification. The system pumps water from the water source to the water purification module 510 to remove chemical contaminants in the fluid in preparation of the dialysate. The water purification module 510 can contain a combination of chemical absorbants, such and activated carbon or other compounds known in the art The sorbent may also contain one or more ion exchange materials that remove ionic species from the water in exchange for $H^+$ or $OH^-$ ions. The system can pump the fluid to a sterilization module 514 for sterilizing the peritoneal dialysate prior to infusion into the patient. The sterilization module 514 can include one or more of a first ultrafilter, a second ultrafilter, and a UV light source, or any combination thereof. The sterilization module can be any component or set of components capable of sterilizing the peritoneal dialysate.

The concentrate sources 512 can contain one or more solutes for generating the peritoneal dialysate from purified water. The concentrates in the concentrate source 512 are utilized to generate a peritoneal dialysis fluid that matches a dialysis prescription, as described. A concentrate pump (not shown) in communication with the processor or computing unit controls the movement of fluid from the concentrate sources 512 into the peritoneal dialysate generation flow path 504. Table 2 provides non-limiting exemplary ranges of commonly used components of peritoneal dialysate. One of skill in the art will understand that alternatives to the components listed in Table 2 can be used. Other osmotic agents can be used in addition to, or in place of, the dextrose, including glucose, icodextrin or amino acid solutions, including dialysate with multiple osmotic agents. Although the sources of sodium, calcium, and magnesium listed in Table 2 are chloride salts, other sodium, magnesium, and calcium salts can be used, such as lactate or acetate salts. Peritoneal dialysate may also contain buffers for maintaining pH of the peritoneal dialysate. Exemplary, non-limiting examples of suitable buffers include bicarbonate buffer, acetate buffer or lactate buffer. Although not generally used in peritoneal dialysis, potassium chloride can be used for hypokalemic patients who don't receive sufficient potassium through diet. The concentrate sources 512 can include any number of concentrates combined or in separate concentrate sources. For example, one or more osmotic agent sources can be included in addition to a single ion concentrate source. Alternatively, multiple ion concentrate sources can be used with each ion concentrate in a separate concentrate source. Any combination of concentrates in any number of concentrate sources can be used with the invention.

TABLE 2

| Component | Concentration |
| --- | --- |
| Sodium chloride | 132-134 mmol/L |
| Calcium chloride dehydrate | 1.25-1.75 mmol/L |
| Magnesium chloride hexahydrate | 0.25-0.75 mmol/L |
| Sodium Lactate | 35-40 mmol/L |
| Dextrose (D-glucose) monohydrate | 0.55-4.25 g/dL |
| pH | 5-6 |
| Osmolality | 346-485 (hypertonic) |

The water source 508, water purification module 510, concentrate source 512, and sterilization module 514 can be fluidly connectable to the integrated cycler 516 for immediate delivery of the generated peritoneal dialysate to the patient. Alternatively, a peritoneal dialysate reservoir (not shown) can be included to collect the generated peritoneal dialysate for later use. One or more processors 522 which can be part of a larger computing device 520, can control the movement of fluid from the concentrate source 512 to the peritoneal dialysate generation flow path 504 based on a peritoneal dialysis prescription 530. The concentrate sources can infuse each particular concentrate to provide an infused ion concentration that is lower than a prescribed amount for a particular patient. One desired outcome can be to provide a concentration for a particular ion that is lower than a patient's pre-dialysis ion concentration. Additionally, if multiple ion sources are to be delivered by a concentrate source, the present system can selectively dilute a desired ion while maintaining concentration levels for other ions. Hence, the present invention can avoid adjusting down every ion insofar as an added diluent may adversely affect concentrations of ions already in a normal range. The processors 522 can also control the pumps in the cycler and a heater (not shown) for heating the peritoneal dialysate prior to infusion. One or more sensors can be included in the peritoneal dialysate generation flow path 504 and/or the infusion line 528 to ensure the therapy delivered to the patient matches the peritoneal dialysis prescription.

Patient parameters can be derived from fluid sampled by one or more sensors 506 when removed or from or introduced into the peritoneal cavity 552 of the patient 550. Patient parameters can also be derived from the patient 550 such as by monitoring blood pressure via a sensor 506 monitoring the patient 550. Patient parameters can also be input into the system 500 as a parameter input 554. A sensor 506 can be positioned in the peritoneal dialysate effluent line 502, the peritoneal dialysate generation flow path 504, or in both the peritoneal dialysate effluent line 502 and the peritoneal dialysate generation flow path 504. A sensor 506 can be connected to the patient 550. For example, a blood pressure sensor can be connected to the patient 550. Patient parameters can be derived using the one or more or more sensors 506. Implantable sensors, such as implantable or wearable cardiac rhythm management systems or other sensors can be in communication with the processors 522 to provide the system with patient parameters. The sensors 506 can be separate sensors, a combined sensor positioned along both the peritoneal dialysate effluent line 502 and the peritoneal dialysate generation flow path 504, or combined or separate sensors along a common peritoneal dialysate effluent line and peritoneal dialysate generation flow path. The sensors 506 can be placed at various locations along the peritoneal dialysate effluent line 502 and the peritoneal dialysate generation flow path 504, including within or between the cycler 516, the water source 508, the water purification module 510, the concentrate source 512, and the sterilization module 514, or between the cycler 516 and the peritoneal cavity 552. The sensors 506 can be posited to take measurements directly from the patient 550.

The one or more sensors 506 can include blood pressure sensor to measure blood pressure of a patient 550 during a session. The sensor 506 can include a flow sensor to measure a volume of fluid removed from a peritoneal cavity 552 of the patient 550. The sensor 506 can include a solute concentration sensor to measure a solute concentration of the fluid removed from the patient. The sensor 506 can include a refractive index sensor to measure glucose or other osmotic agent concentration in the fluid removed from the patient. The sensor 506 can include a conductivity sensor or ion selective electrodes to measure conductivity or solute concentration of the fluid removed from the patient. The sensor 506 can include a pressure sensor to measure a pressure of fluid removed from a patient. The sensor 506 can include a temperature sensor to measure a temperature of fluid removed from a patient.

The computing device 520 can include the one or more processors 522, memory 524, and one or more input/output interfaces 526. The memory 524 can be in communication with the processor 522 and store instructions that when executed perform the methods described herein. The input/output interfaces 526 can include an input interface to receive parameter input 554, an input interface to receive inter-session history 556 of the patient, an input port to receive information from the one or more sensors 506, and an output port to output control signals implementing dialysis parameters (with or without adjustment) for a subsequent session. The processor 522 can be in communication with the at least one sensor 506. As with all features of the present application, intervening components (such as the input/output interface 526) can be present between the processor 522 and the sensor 506. The computing device 520 can be a stand-alone device independent of the integrated cycler 516, or can be a part of the integrated cycler 516. The computing device 520 can be a remote device in network communication with the sensor 506, such as via the Internet, or connected wirelessly.

An alternative system for monitoring patient parameters during a peritoneal dialysis session to make modifications within the peritoneal dialysis session can include a peritoneal dialysate regeneration module, a pump, and an infusion line. The infusion line can be fluidly connected to the peritoneal dialysate generation flow path 504 downstream of the sterilization module 514. The peritoneal dialysate effluent line 502 can be fluidly connected to the peritoneal dialysate generation flow path 504 upstream of the peritoneal dialysate regeneration module. The peritoneal dialysate regeneration module can include a sorbent cartridge, an electrodialysis unit, one or more ultrafilters, or any other combination of components for removal of contaminants from the dialysate removed from the patient. The used peritoneal dialysate, after regeneration, can be pumped back into the peritoneal dialysate generation flow path 504 for reuse.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A computer implemented method, comprising the steps of:
    receiving one or more patient parameters before the start of a current peritoneal dialysis session;
    receiving a prior peritoneal dialysis prescription from a prior peritoneal dialysis session; and
    storing the one or more patient parameters before the start of the current peritoneal dialysis session and the prior peritoneal dialysis prescription into a machine-readable storage medium for storing instructions, which when executed by a dialysis machine performs the steps of:
    determining a new peritoneal dialysis prescription based on adjustments of the prior peritoneal dialysis prescription based on the one or more patient parameters before the start of the current peritoneal dialysis session; and
    delivering the new peritoneal dialysis prescription for a current peritoneal dialysis therapy to a patient in need thereof, using the dialysis machine; and further comprising at least one of:
    a) receiving an effluent pH from a first dialysis session; receiving an effluent pH from at least a second dialysis session; trending the effluent pH over the first and second dialysis sessions; and providing an alert if a trend of effluent pH changes by greater than a predetermined threshold;
    b) receiving an effluent color and clarity from a first dialysis session; receiving an effluent color and clarity from at least a second dialysis session; trending the effluent color and clarity over the first and second dialysis sessions; and providing an alert if a trend of effluent color and clarity changes by greater than a predetermined threshold; and
    c) receiving an intraperitoneal pressure from a first dialysis session; receiving an intraperitoneal pressure from at least a second dialysis session; trending the intraperitoneal pressure over the first and second dialysis sessions; and adjusting a dwell time if the intraperitoneal pressure changes by greater than a predetermined threshold between the first and second dialysis sessions.

2. The computer implemented method of claim 1, wherein the one or more patient parameters comprise one or more of the following:
    i) a patient weight loss;
    ii) a patient blood pressure change;
    iii) a fluid removal volume;
    iv) a patient goal;
    v) an effluent pH;
    vi) an effluent color and clarity;
    vii) an effluent temperature;
    viii) a patient posture;
    ix) an intersession history;
    x) an intraperitoneal pressure; and
    xi) a membrane transfer efficiency.

3. The computer implemented method of claim 2, wherein the step of determining a new peritoneal dialysis prescription comprises the step of reducing an osmotic agent concentration, reducing a dwell time, and/or reducing a number of cycles if the patient blood pressure change exceeds a predetermined threshold.

4. The method of claim 1, wherein the new peritoneal dialysis prescription includes at least one of:
    i) a number of cycles;
    ii) a dialysate temperature;
    iii) a target fluid removal volume;
    iv) a cycle volume;
    v) a dwell time;
    vi) an osmotic agent concentration; and
    vii) a solute concentration.

5. The computer implemented method of claim 1, wherein at least one patient parameter is received from an implantable or wearable sensor.

6. The computer implemented method of claim 1, wherein the one or more patient parameters comprise at least an intersession history; wherein the intersession history includes one or more of a peritoneal dialysate composition, a target fluid removal volume and a fluid removal volume, a dwell time, a number of cycles, a cycle volume, a patient activity, and a patient well-being.

7. The computer implemented method of claim 1, wherein the one or more patient parameters comprise at least a patient well-being, wherein the patient well-being includes whether the patient experienced cramping during or after a previous dialysis session; and wherein the adjustments of the prior peritoneal dialysis prescription comprise increasing a solute concentration of at least one solute if the patient experienced cramping during or after the previous dialysis session.

8. The computer implemented method of claim 1, wherein the one or more patient parameters comprise at least patient well-being; wherein the patient well-being includes whether the patient experienced edema during or after a previous dialysis session; and wherein the adjustments of the prior peritoneal dialysis prescription comprise increasing an osmotic agent concentration, increasing a dwell time, and/or increasing a number of cycles if the patient experienced edema during or after the previous dialysis session.

9. The computer implemented method of claim 1, wherein the one or more patient parameters include a fluid removal volume; the new peritoneal dialysis prescription includes a target fluid removal volume; and the method further comprises the step of adjusting an osmotic agent concentration, a dwell time, a number of cycles, or combinations thereof, in response to a difference between the fluid removal volume and the target fluid removal volume.

10. The computer implemented method of claim 9, wherein the step of determining a new peritoneal dialysis prescription comprises the step of increasing an osmotic agent concentration, increasing a dwell time, and/or increasing a number of cycles if the fluid removal volume is less than the target fluid removal volume; and wherein the step of determining a new peritoneal dialysis prescription comprises the step of decreasing an osmotic agent concentration, decreasing a dwell time, and/or decreasing a number of cycles if the fluid removal volume is greater than the target fluid removal volume.

11. The computer implemented method of claim 1, wherein the one or more patient parameters comprise at least a fluid removal volume; and wherein the fluid removal volume is determined by the patient weight loss.

12. The computer implemented method of claim 1, wherein the step of delivering the new peritoneal prescription to a patient comprises:

controlling the movement of a fluid from a water source to an infusion line of an integrated cycler in a peritoneal dialysate generation flow path;

controlling the movement of a fluid from one or more concentrate sources to the peritoneal dialysate generation flow path to generate a peritoneal dialysate;

sterilizing the peritoneal dialysate with a sterilization module;

infusing the peritoneal dialysate into a patient with the integrated cycler; and removing the peritoneal dialysate from the patient through an effluent line.

13. A system, comprising:

a peritoneal dialysate generation flow path having (i) a water source fluidly connectable to the peritoneal dialysate generation flow path; (ii) one or more water purification modules fluidly connectable to the peritoneal dialysate generation flow path; (iii) one or more concentrate sources fluidly connectable to the peritoneal dialysate generation flow path; the one or more concentrate sources containing one or more solutes and including at least an osmotic agent source and an ion concentrate source; (iv) at least one concentrate pump; the concentrate pump controlling the movement of fluid from the one or more concentrate sources to the peritoneal dialysate generation flow path; and (v) a sterilization module fluidly connectable to the peritoneal dialysate generation flow path;

an integrated cycler fluidly connected to the peritoneal dialysate generation flow path; the integrated cycler having at least an infusion line and an effluent line; and a processor; the processor performing the method of claim 1, and controlling the concentrate pump and integrated cycler based on the new peritoneal dialysis prescription.

14. The system of claim 13, further comprising at least one pump positioned in the infusion line and effluent line; the pump in communication with the processor.

15. The system of claim 14, the processor controlling the pump to infuse peritoneal dialysate from the infusion line into a peritoneal cavity of a patient based on the new peritoneal dialysis prescription.

16. The system of claim 13, the processor comprising one or more input/output interfaces for receiving the one or more patient parameters.

17. The system of claim 13, further comprising a peritoneal dialysate regeneration module fluidly connected to the effluent line and the peritoneal dialysate generation flow path.

* * * * *